(12) United States Patent
Andersen et al.

(10) Patent No.: US 11,583,251 B2
(45) Date of Patent: Feb. 21, 2023

(54) US IMAGING PROBE WITH AN US TRANSDUCER ARRAY AND AN INTEGRATED OPTICAL IMAGING SUB-SYSTEM

(71) Applicant: B-K Medical Aps, Herlev (DK)

(72) Inventors: Marianne Andersen, Helsinge (DK); Terry A. Kling, Port Matilda, PA (US); Henrik Jensen, Bagsvaerd (DK); Johannes Paede, Hamburg (DE)

(73) Assignee: BK MEDICAL APS, Herlev (DK)

( * ) Notice: Subject to any disclaimer, the term of this patent is extended or adjusted under 35 U.S.C. 154(b) by 1307 days.

(21) Appl. No.: 15/737,927

(22) PCT Filed: Jun. 22, 2015

(86) PCT No.: PCT/IB2015/054674
§ 371 (c)(1),
(2) Date: Dec. 19, 2017

(87) PCT Pub. No.: WO2016/207692
PCT Pub. Date: Dec. 29, 2016

(65) Prior Publication Data
US 2018/0185008 A1 Jul. 5, 2018

(51) Int. Cl.
*A61B 8/00* (2006.01)
*A61B 1/05* (2006.01)
(Continued)

(52) U.S. Cl.
CPC .............. *A61B 8/4416* (2013.01); *A61B 1/05* (2013.01); *A61B 1/0676* (2013.01);
(Continued)

(58) Field of Classification Search
None
See application file for complete search history.

(56) References Cited

U.S. PATENT DOCUMENTS 4,327,738 A * 5/1982 Green .................... A61B 1/042
348/65
4,375,818 A * 3/1983 Suwaki .............. A61B 1/00177
600/101

(Continued)

OTHER PUBLICATIONS

International Search Report for PCT/IB2015/054674 published as WO2016/207692A1 dated Dec. 29, 2016.
(Continued)

*Primary Examiner* — Katherine L Fernandez
*Assistant Examiner* — Farouk A Bruce
(74) *Attorney, Agent, or Firm* — Daugherty & Del Zoppo, Co. LPA

(57) ABSTRACT

An ultrasound imaging probe (204) includes a transducer array (210). The transducer array includes one or more transducer elements (212). The ultrasound imaging probe further includes an illumination component (218) and an optical imaging component (220). The ultrasound imaging probe further includes an elongated housing (302) with a long axis (304). The elongated housing includes a proximal end region (306) affixed to a handle (308) and a distal end region (310) with a tip region (312). The elongated housing houses the transducer array, the illumination component, and the optical imaging component in the distal end region.

20 Claims, 5 Drawing Sheets

(51) Int. Cl.
*A61B 1/06* (2006.01)
*A61B 8/12* (2006.01)
*A61B 8/08* (2006.01)
*A61B 1/07* (2006.01)

(52) U.S. Cl.
CPC .............. *A61B 1/0684* (2013.01); *A61B 1/07* (2013.01); *A61B 8/12* (2013.01); *A61B 8/445* (2013.01); *A61B 8/4461* (2013.01); *A61B 8/4488* (2013.01); *A61B 8/463* (2013.01); *A61B 8/5261* (2013.01); *A61B 8/56* (2013.01); *A61B 1/0607* (2013.01); *A61B 1/0623* (2013.01)

(56) References Cited

U.S. PATENT DOCUMENTS

| | | | |
|---|---|---|---|
| 4,928,669 | A | 5/1990 | Tsuguhisa |
| 5,800,341 | A | 9/1998 | McKenna |
| 8,267,853 | B2 | 9/2012 | Fisher et al. |
| 2007/0021738 | A1 | 1/2007 | Hasser et al. |
| 2010/0130880 | A1* | 5/2010 | Li ........................ A61B 5/0086 600/504 |
| 2011/0190579 | A1* | 8/2011 | Ziarno ................ G06F 19/3418 600/109 |
| 2011/0193948 | A1* | 8/2011 | Amling .............. A61B 1/00059 348/68 |
| 2014/0187958 | A1* | 7/2014 | Boutet ................ A61B 8/4483 600/462 |
| 2014/0187961 | A1 | 7/2014 | Yamakoshi |
| 2015/0051485 | A1* | 2/2015 | Itoh .................... A61B 1/00096 600/427 |
| 2015/0272445 | A1* | 10/2015 | Rozental .............. A61B 8/445 600/407 |

OTHER PUBLICATIONS

BK Medical type 2052 Product Data brochure for Anorectal 3D transducer, dated Mar. 2012.
Stark, et al., Natural Orifice Surgery: Transdouglas Surgery—A New Concep, Scientific Paper JSLS (2008) 12:295-298.
Olympus Peripheral Diagnostic Flyer, E042871O, 1.000, Aug. 2014.
Olympus, Endoscopic Ultrasound pamphlet, Feb. 26, 2015.
BK Medical Product Catalog, Oct. 12, 2011.
Olympus, UM-S20-20R, Ultrasonic Probe product brochure.
Olympus Medical Systems, UM-BS20-26R, UM-S30-20R/UM-S30-25R, UM-S20-17S/UM-S20-20R and UM-2R/UM-3R—A wide range of Ultrasonic Probes brochure.

* cited by examiner

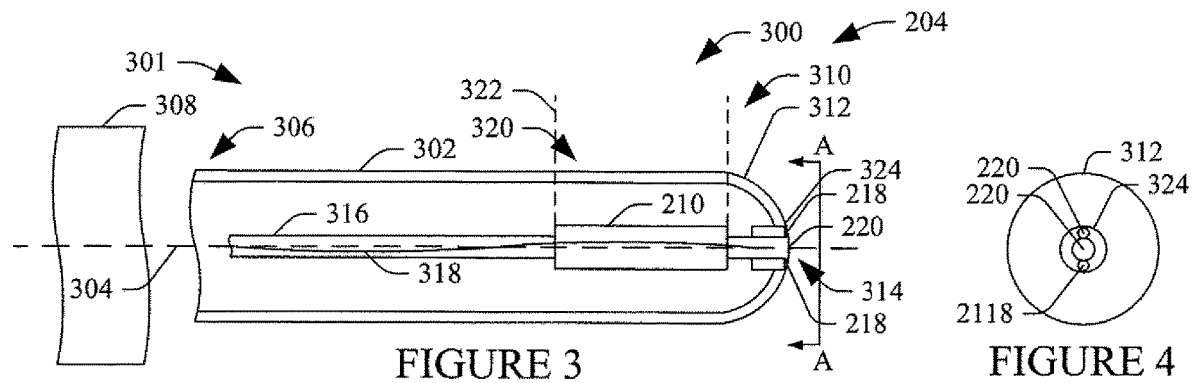
FIGURE 3
FIGURE 4
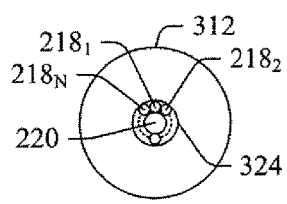
FIGURE 5
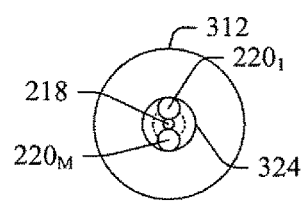
FIGURE 6
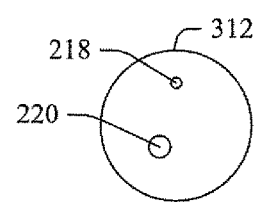
FIGURE 7
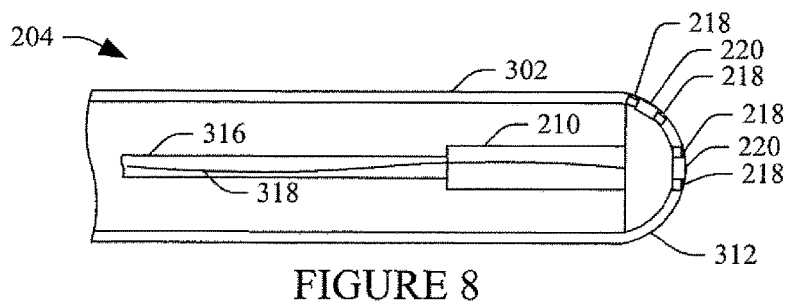
FIGURE 8
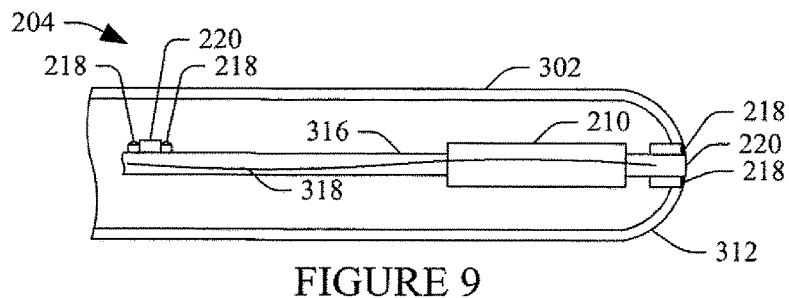
FIGURE 9

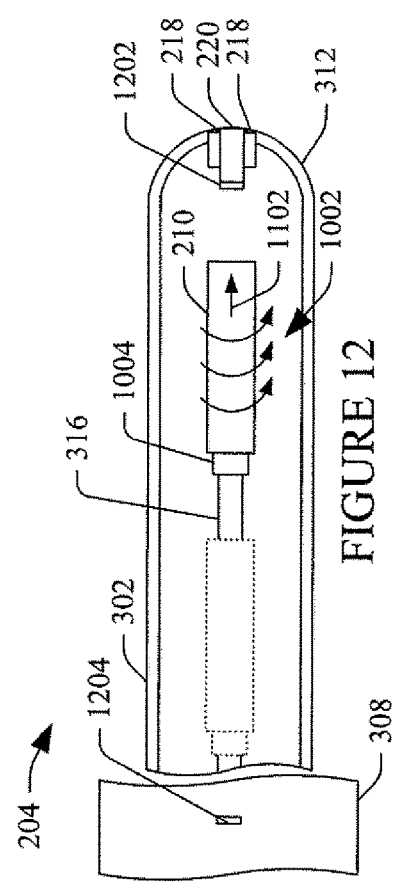
FIGURE 10B
FIGURE 10A
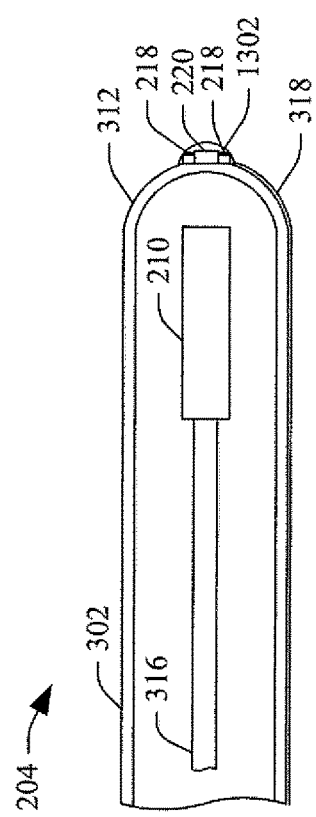
FIGURE 12
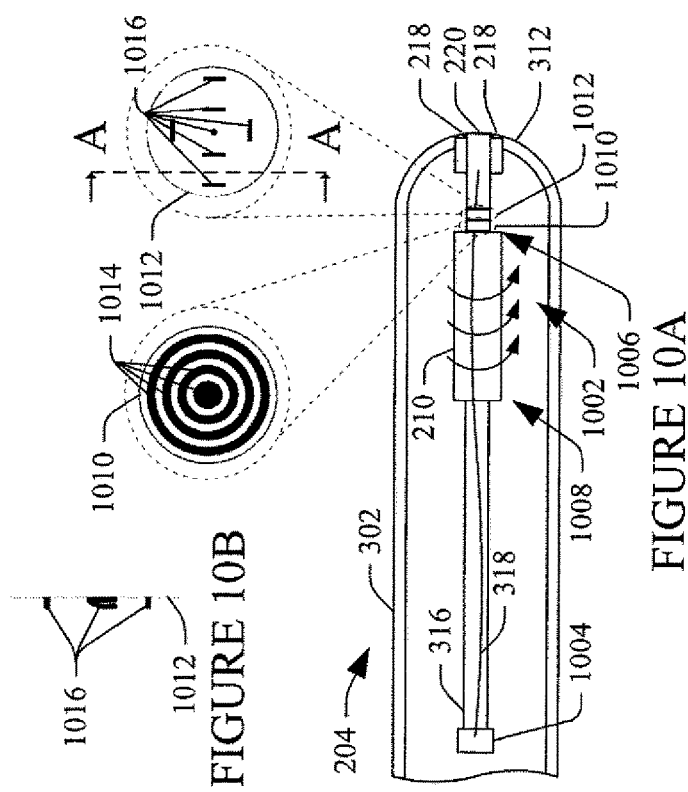
FIGURE 11
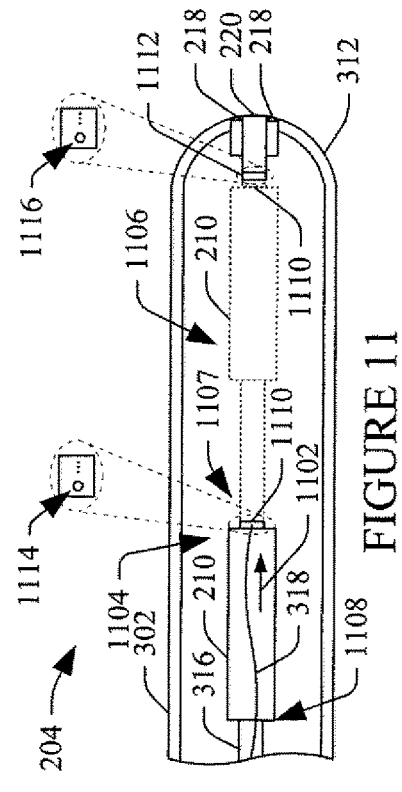
FIGURE 13

US IMAGING PROBE WITH AN US TRANSDUCER ARRAY AND AN INTEGRATED OPTICAL IMAGING SUB-SYSTEM

RELATED APPLICATION

This application is a national filing of PCT application Serial No. PCT/IB2015/054674, filed Jun. 22, 2015, published as WO2016/207692 on Dec. 29, 2016. This application claims priority to PCT application Serial No. PCT/IB2015/054674, published as WO2016/207692 on Dec. 29, 2016.

TECHNICAL FIELD

The following generally relates to an ultrasound imaging probe and more particularly to an ultrasound imaging probe with a housing that houses an ultrasound imaging transducer array and an integrated optical imaging sub-system.

BACKGROUND

Ultrasound (US) imaging has provided useful information about the interior characteristics (e.g., organ tissue, blood flow, other flow, etc.) of a subject or object under examination. A general ultrasound imaging system has included an ultrasound probe with a transducer array and a console. The ultrasound probe houses a transducer array, and the console includes a display monitor and a user interface. The transducer array transmits an ultrasound signal into a field of view and receives echoes produced in response to the signal interacting with structure therein. The echoes are processed, producing an image of the scanned structure, which is visually presented through the display monitor.

Endoscopic ultrasound combines ultrasonography and endoscopy. The particular type of endoscope used depends on the site in the body and the type of procedure. For example, colorectal examinations to identify cancerous and pre-cancerous regions have used a sigmoidoscope, a proctoscope, etc. with a light and an optical imager at the distal end. For the exam, the scope is inserted and used for initial visual identification of polyps or superficial cancers on the rectal wall tissue. The location of such a region of interest is determined, and the scope is removed. The US probe is then inserted to the same position for an ultrasound scan and evaluation of the region of interest.

An endoscopic probe has also been configured to also support an ultrasound probe. FIG. 1 shows a rendering of such an endoscopic probe from Olympus. In FIG. 1, an endoscopic probe 102 includes a light source 104 and an optical imager 106 at a distal end 108. The endoscopic probe 102 further includes an instrument channel 110, which extends the length of the endoscopic ultrasound probe. With this example, the endoscopic probe 102 is inserted and used as discussed above. However, rather than removing the endoscope and inserting an ultrasound probe, an ultrasound mini-probe 112 protruding from the channel 110 out of the distal end 108 is used.

Unfortunately, such probes require feeding the ultrasound mini-probe through the channel, which consumes time and may require an additional hand while keeping the light source and the optical imager directed on the target tissue of interest. Furthermore, the light source and the optical imaging component are at the distal end of the endoscopic probe. As a consequence, the ultrasound mini-probe may partially obstruct the light and view and/or it may not be possible to see what is beyond the end of the ultrasound mini-probe when the ultrasound mini-probe is installed and protruding from the channel. As such, there is an unresolved need for another approach.

SUMMARY

Aspects of the application address the above matters, and others.

In one aspect, an ultrasound imaging probe includes a transducer array. The transducer array includes one or more transducer elements. The ultrasound imaging probe further includes an illumination component and an optical imaging component. The ultrasound imaging probe further includes an elongated housing with a long axis. The elongated housing includes a proximal end region affixed to a handle and a distal end region with a tip region. The elongated housing houses the transducer array, the illumination component, and the optical imaging component in the distal end region.

In another aspect, a method includes receiving a first signal activating a light source and an optical sensor disposed in an ultrasound imaging section of an ultrasound probe in a cavity. The method further includes acquiring optical data of a field of view in the cavity with the optical sensor, wherein the field of view is illuminated by light from the light source. The method further includes generating an optical image with the optical data, wherein the optical image shows tissue of interest in the field of view and displaying the optical image. The method further includes receiving a second signal activating an ultrasound transducer array disposed in the ultrasound imaging region of the ultrasound probe. The method further includes acquiring ultrasound data of the tissue of interest in the field of view in the cavity with a transducer array disposed in the ultrasound imaging region of the ultrasound probe. The method further includes generating an ultrasound image with the ultrasound data and displaying the ultrasound image.

In another aspect, an endocavitary volumetric transducer includes a handle and a cable extending from the handle and including an interface to an ultrasound system at an end region of the cable. The endocavitary volumetric transducer further includes a shaft extending from an opposing end of the handle and including a first proximal region affixed to the handle and a second distal region. The second distal region includes an acoustic window and encloses a transducer array, a light, and an optical imager.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 3 schematically illustrates a side view of an example of an imaging portion of the probe;

FIG. 4 schematically illustrates an example front view of the probe of FIG. 3;

FIG. 5 illustrates an example front view of a variation of the probe of FIG. 3 with a different location and/or number of the illumination component and the optical imaging component;

FIG. 6 illustrates an example front view of another variation of the probe of FIG. 3 with a different location and/or number of the illumination component and the optical imaging component;

FIG. 7 illustrates an example front view of still another variation of the probe of FIG. 3 with a different location and/or number of the illumination component and the optical imaging component;

FIG. 8 illustrates a variation of the imaging portion of the probe of FIG. 3 with an additional illumination component in the tip;

FIG. 9 illustrates another variation of the imaging portion of the probe of FIG. 3 with an additional illumination component outside of the tip;

FIG. 10A illustrates a variation of the probe of FIG. 3 with a rotating transducer array;

FIG. 10B illustrates a cross sectional view of one of the optical component circuit of FIG. 10A along line A-A;

FIG. 11 illustrates a variation of the probe of FIG. 3 with a translating transducer array;

FIG. 12 illustrates a variation of the probe of FIG. 3 with a rotating and translating transducer array;

FIG. 13 illustrates a variation of the probe of FIG. 3 with the illumination component and the optical imaging component disposed outside of the housing;

DETAILED DESCRIPTION

Figure 1:
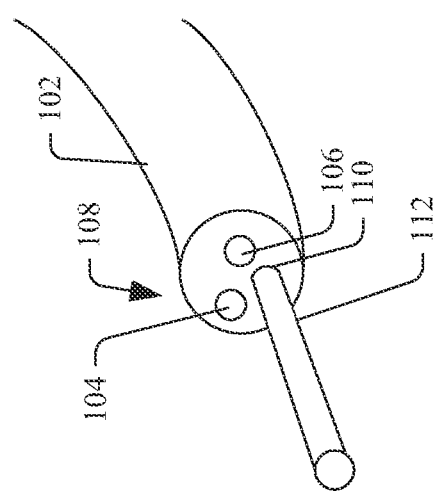
FIG. 1 illustrates a prior art endoscope configured to support an ultrasound probe feed through an instrument channel thereof.
Figure 2:
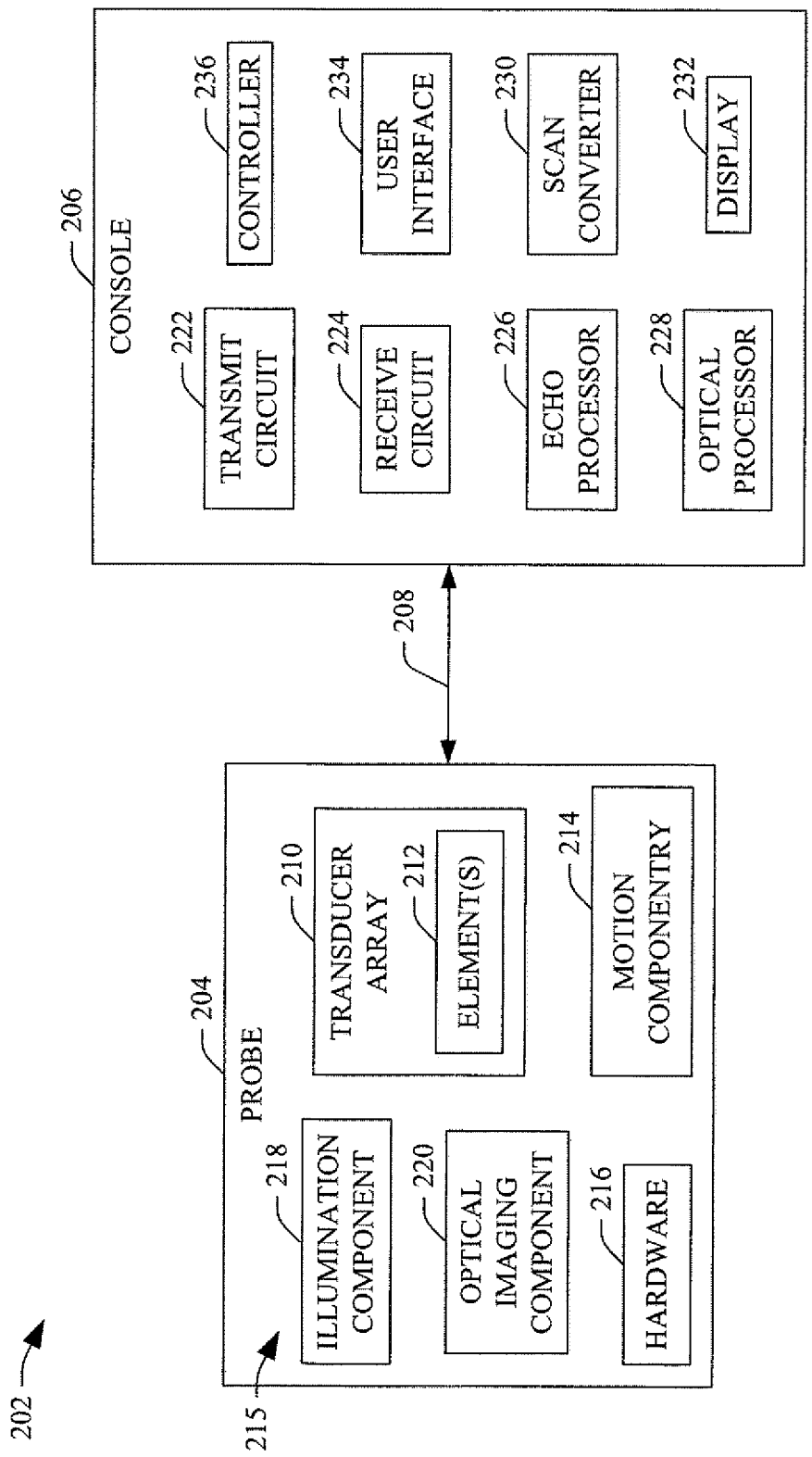
FIG. 2 schematically illustrates an example ultrasound imaging system with a probe with a housing and a transducer array, an illumination component, and an optical imaging component disposed within the same housing.

FIG. 2 schematically illustrates an imaging system 202 such as ultrasound imaging system. The imaging system 202 includes an ultrasound imaging probe 204 and a console 206. The ultrasound imaging probe 204 and the console 206 include complementary communication interfaces, which are configured for wireless and/or wired communication between the ultrasound imaging probe 204 and the console 206 over a communication path 208.

The ultrasound imaging probe 204 includes a transducer array 210 with a one-dimensional (1-D) of one or more transducer elements 212 or a two-dimensional (2-D) array of the transducer elements 212. The transducer elements 212 are configured to transmit ultrasound signals and receive echo signals. Suitable configurations include, but are not limited to, single element, linear array, curved array, phased array, etc. The transducer array 210 can be fully populated or sparse, square, circular, irregular, etc. The illustrated probe 204 further includes motion componentry 214. In one instance, the motion componentry 214 is configured to translate, rotate and/or otherwise move the transducer array 210 within the probe. Translational and/or rotational motion can be achieved through mechanical and/or electrical components. Such motion allows volumetric (3-D) imaging with a 1-D array or a 2-D array.

The ultrasound imaging probe 204, in one instance, is configured as a natural orifice probe, which includes probes configured for insertion into a cavity of the body by way of a natural orifice of the body (e.g., anus, vagina, esophagus, eye, ear, nasal cavity, etc.). Additionally or alternatively, the probe 204 is configured for insertion through a non-natural orifice of the body (e.g., an incision). Examples of suitable probes include, but are not limited to, the Type 2052 Anorectal 3D transducer with mechanical rotating crystals and the Type 8838 3DART™ 8838 ultrasound transducer with electronic steering, both products of BK-Medical ApS, a company of Herlev, DK, which is a wholly owned subsidiary of Analogic Corporation, a company of Massachusetts, USA. Such probes are used for colorectal and/or other examinations. Other probes are also contemplated herein. In a variation, the motion componentry 214 is omitted.

The ultrasound imaging probe 204 further includes an optical portion 215 with supporting hardware 216. The portion 215 includes an illumination component 218 and an optical imaging component 220. Examples of the illumination component 218 include a light emitting diode(s), a laser, an optical fiber, etc. Examples of the optical imaging component 220 include a camera, a video camera, a lens, an optical fiber, etc. The illumination component 218 provides light for the optical imaging component 220. As described in greater detail below, in one non-limiting instance, the illumination component 218 and the optical imaging component 220 are both housed inside of a housing of the probe 204. In this configuration, the illumination component 218 and the imaging component 220 are arranged such that the optical imaging component 220 images structure illuminated and identified with the optical portion. The probe 204 can be considered an endocavitary US transducer with optical examination componentry.

Disposing the illumination and optical imaging components 218 and 220 as such in a known relation to the transducer array 210 provides a more accurate relationship of the two types of images (optical and ultrasound) of a region of interest while they are being gathered. It also provides the opportunity to switch back and forth between imaging modalities or the simultaneous collection of video and ultrasound images. Such a configuration also mitigates having to feed the transducer array 210 through a channel of the probe, reducing procedure complexity and saving time. Furthermore, patient comfort can be improved by reducing the number of inserted instruments, and procedure time can also be reduced. Also described in greater detail below, the illumination component 218 and the optical imaging component 220 can be physically arranged within the probe 204 so that the illumination component 218 can be used to illuminate tissue without interfering with the transducer array 210 and vice versa.

The console 206 includes transmit circuitry 222. The transmit circuitry 222 generates a set of radio frequency (RF) pulses that are conveyed to the transducer array 210. The set of pulses actuates a corresponding set of the transducer elements 212, causing one or more sets of the elements 212 to transmit ultrasound signals into an examination or scan field of view. The console 206 further includes receive circuitry 224. The receive circuitry 224 receives echoes (RF signals) generated in response to the transmitted ultrasound signals from the transducer array 210. The echoes, generally, are a result of the interaction between the emitted ultrasound signals and the structure (e.g., flowing blood cells, organ cells, etc.) in the scan field of view. A switch may be configured to switch between the transmit circuitry 222 and the receive circuitry 224 for transmit and receive operations.

The console 206 further includes an echo processor 226 that processes received echoes. Such processing may include applying time delays, weighting on the channels, summing, and/or otherwise beamforming received echoes.

Other processing may lower speckle, improve specular reflector delineation, and/or includes FIR filtering, IIR filtering, etc. For B-mode, the echo processor 226 generates a sequence of focused, coherent echo samples along focused scanlines of a scanplane. The console 206 further includes a scan converter 230 that scan converts (using analog and/or digital scan converting techniques) the frames of data to generate data for display, for example, by converting the data to the coordinate system of a display 232, which may be integrated with the console (as shown) or a separate device therefrom.

In the illustrated embodiment, the console 206 further includes an optical processor 228 that processes the information from the optical imaging component 220 to generate optical images for display via the display 232 and/or other display. In a variation, the optical processor 228 is located external to the console 206, for example, in another computing device. In another variation, the optical processor 228 is implemented by a set of processors distributed across computing device. In another variation, the optical processor 228 is provided through h a "cloud" based service. With a cloud based service, the service can provide storage and/or processing resources. The above are non-limiting example, and it is to be understood that the optical processor 228 can be elsewhere located and/or implemented.

The console 206 further includes a user interface (UI) 234 with one or more input devices (e.g., a button, a knob, a touchscreen, etc.) and/or one or more output devices (e.g., the display 232, communication ports, etc.), which allows for interaction with the system 202. The console 206 further includes a controller 236 that controls at least one of transducer array 210, the element(s) 212, the motion componentry 214, the illumination component 218, the optical imaging component 220, the transmit circuit 222, the receive circuit 224, the echo processor 226, the optical processor 228, the scan converter 230, the display 232 or the user interface 234. At least one of the components of the console 206 can be implemented by a processor (e.g., a microprocessor, a central processing unit, etc.) executing computer readable instructions encoded, embedded, stored, etc. on non-transitory computer readable storage medium such as physical memory.

FIG. 3 illustrates a non-limiting example of a sub-portion of an imaging section 300 of a shaft 301 of the probe 204. The illustrated sub-portion includes an elongated housing 302 with a long axis 304, a proximal end region 306 disposed by a handle region 308, and a distal end region 310 with a tip region 312. The housing 302 houses the transducer array 210, which, in this example, is fixed at a static location in the housing 302. The illustrated housing 302 also houses the illumination component 218 and the optical imaging component 220. In this example, the optical imaging component 220 is disposed on the long axis at about a center region 314 of the tip region 312, and the illumination component 218 is disposed about an outer perimeter of the optical imaging component 220. A conduit 316 extends through the housing 302 between the end regions 306 and 310, and a set of electrically conductive members (e.g., a wire or the like) and/or optical routing members (e.g., a fiber optic such as an optical fiber, a bundle of optical fibers, etc.), referred to herein as members 318, is routed there through.

The members 318 provide a path or pathway from the handle 308 to the tip region 312. This pathway can be configured to route all electrical signals (e.g., power, control, electrical transmission of optical information, etc.) and/or optical signals between the handle 308 to the tip region 312. In one instance, one or more of the members 318 supply energy to the illumination component 218 in response to a signal activating the illumination component 218. The energy is removed from the illumination component 218 in response to a signal deactivating an activated illumination component 218. Where the optical imaging component 220 includes a still camera, a video camera or the like, one or more of the members 318 supplies energy to the optical component 220, conveys "on" and "off" command signals thereto, and routes electrical and/or optical signals generated thereby to the console 206. Where the optical imaging component 220 includes a fiber optic(s), one or more of the members 318 includes the fiber optic(s). In this instance, the componentry to activate and deactivate the fiber optic(s) is located outside of the tip region 312, for example, in the housing 308, in the handle region 308, and/or elsewhere in the probe 204 and/or console 206.

One or more of the members 318 or other member may convey a signal to and from the transducer array 210 and/or other components of the probe 204. At least a sub-area 320 of the housing 302, e.g., a sub-area through which an ultrasound signal 322 produced by the transducer array 210 are transmitted and echo signals are received, includes an acoustic material. At least a portion of the tip region 312 includes a support 324 for the illumination component 218 and the optical imaging component 220. Turning to FIG. 4, a non-limiting example of the tip region 312 is illustrated. FIG. 4 depicts a view along a line A-A of FIG. 3 looking into the tip region 312 showing the support 324, the illumination component 218, the optical imaging component 220, and the tip region 312. In this example, the optical imaging component 220 includes a single optical imaging component 220 surrounded by two illumination components 218 disposed on opposing sides of the optical imaging component 220. The transducer array 210 can be a single element, 1-D array, or a 2-D array transducer.

Turning to FIG. 5, another example includes N illumination components 218, where N is an integer equal to or greater than one, including illumination components $218_1$, $218_2$, . . . , $218_N$. In one instance, the N illumination components 218 may extend entirely around the optical imaging component 220, with neighboring illumination components 218 in physical contact or close physical vicinity. In another instance, the N illumination components 218 may be spaced apart from each other, e.g., by at least a distance on an order of a size of a diameter of an illumination component 218. In another instance, the N illumination components 218 may be spaced apart by a distance therebetween. Where N>2, the illumination components 218 can be disposed symmetrically or asymmetrically about the optical imaging component 220. Furthermore, at least two of the illumination components 218 may provide a different size, color, power, and/or other characteristic.

Next at FIG. 6, the probe 204 includes a single illumination component 218 centered at the tip region 312 with M optical imaging components 220 disposed around the illumination component 218. Similarly, M imaging components 220 may extend entirely around the illumination component 218, with neighboring optical imaging components 220 in physical contact or close physical vicinity. In another instance, the M optical imaging components 220 may be spaced apart from each other, e.g., by at least a distance on an order of a size of a diameter of an optical imaging components 220. In another instance, the M optical imaging components 220 may be spaced apart by a distance therebetween. Where M>2, the optical imaging components 220 can be disposed symmetrically or asymmetrically about the illumination component 218. Furthermore, at least two of the optical imaging components 220 may provide a different field of view, focus, focal point, and/or other optical characteristic.

FIG. 7 shows another example in which neither illumination component 218 nor the optical imaging component 220 are at the center. The location shown in this example is not limiting, and neither illumination component 218 and/or the optical imaging component 220 can be disposed elsewhere. Although FIGS. 3-7 show the optical imaging component 220 having a larger diameter than the illumination component 218, the can have a same size or the optical imaging component 220 can have a smaller diameter than the illumination component 218. Furthermore, the shape of the illustrated optical imaging component 220 and/or illumination component 218 are non-limiting. For example, the shapes can alternatively be square, rectangular, elliptical, irregular, and/or other non-circular shape.

Turning to FIG. 8, another example of the sub-portion of the imaging section 300 of the shaft 301 of the probe 204 is illustrated. In this example, at least a second optical imaging set, including at least a second optical imaging component 220 and at least another two of the illumination components 218, is disposed in the tip region 312. The different optical imaging sets are configured to capture data for different views. Such views can be fully overlapping, partially overlapping or non-overlapping. FIG. 9 shows yet another example of the sub-portion of the imaging section 300 of the shaft 301 of the probe 204. In this example, at least a second optical imaging set, including at least a second optical imaging component 220 and at least another two of the illumination components 218, is disposed in the housing 302 but not within the tip region 312. Likewise, the different optical imaging sets can be configured to capture data for different views, including fully overlapping, partially overlapping or non-overlapping views. Other numbers of optical imaging sets and/or locations are contemplated herein.

FIG. 10A shows an example of the probe 204 in which transducer array 210 is configured therein for mechanical rotational motion 1002. In this instance, the transducer array 210 is affixed to the conduit 316, which is affixed to a rotating member 1004. In another embodiment, the transducer array 210 can be directly affixed to the rotating member 1004, e.g., when the rotating member 1004 is disposed between the conduit 316 and the transducer array 210. In another instance, more than one component (i.e., more than just the conduit 316) may be disposed between the rotating member 1004 and the transducer array 210. The rotating member 1004 may be configured to rotate the transducer array 210 about the long axis in one direction (e.g., clockwise or counter-clockwise) or two directions (e.g., clockwise and counter-clockwise), through a range of less 360 degrees, 360 degrees, or more than 360 degrees. The members 318 still route through the conduit 316.

In FIG. 10A, a distal end region 1006 of the transducer array 210, which opposes an end region 1008 of the transducer array 210 coupled to the conduit 316, includes a circuit 1010 or the like, to which the members 318 interface. A complementary circuit 1012 is coupled with the optical imaging component 220 and the illumination component 218. In this example, the circuit 1010 includes concentric conductive rings 1014, and the complementary circuit 1012 includes conductive raised contacts 1016 (e.g., spring contacts, pads, etc.). FIG. 10B illustrates a cross sectional view of one of the complementary circuit 1012 of FIG. 10A along line A-A, showing the includes conductive raised contacts 1016. The complementary contacts 1014 on the circuit 1010 and contacts 1016 the complementary circuit 1012 interface when the transducer array 210 is rotating and when the transducer array 210 is not rotating, and the optical imaging component 220 and the illumination component 218 are controlled as described herein. This includes routing electrical and/or optical information of the illumination component 218 and/or the optical imaging component 220 between respective complementary contacts 1014 and 1016 of the circuits 1010 and 1012. The circuits 1010 and/or 1012 may include printed circuit boards (PCB's), wire wrap, etc. Other circuit configurations are also contemplated herein.

FIG. 11 shows an example of the probe 204 in which transducer array 210 is configured therein for mechanical translation 1102. In this instance, the conduit 316 is extendable between at least a first location 1104 and a second location 1106. A distal end region 1107 of the transducer array 210, which opposes an end region 1108 of the transducer array 210 coupled to the conduit 316, includes a circuit 1110 or the like, to which the members 318 interface. A complementary circuit 1112 is coupled with the optical imaging component 220 and the illumination component 218. In this configuration, when the transducer array 210 is in the fully extended position, the complementary contacts 1114 on the circuit 1110 and contacts 1116 the complementary circuit 1112 interface, and the optical imaging component 220 and the illumination component 218 are controlled as described herein. As discussed herein, this includes routing electrical and/or optical information of the illumination component 218 and/or the optical imaging component 220 between respective complementary contacts 1114 and 1116 of the circuits 1110 and 1112. Otherwise, the complementary contacts do not interface. The circuits 1110 and/or 1112, similar to circuits 1010 and/or 1012, may include printed circuit boards (PCB's), wire wrap, etc. Other circuit configurations are also contemplated herein.

FIG. 12 illustrates an example of the probe 204 which is a combination of the examples of FIGS. 10 and 11, and the transducer array 210 is configured to both translate and rotate, individually and/or concurrently. In this example, complementary wireless interfaces 1202 and 1204 are located in the tip region 312 and the handle region 308, and the optical imaging component 220 and the illumination component 218 communicate there through. The complementary wireless interface 1204 could be otherwise located, e.g., in the housing 302, in the console 206, and/or elsewhere. In a variation, the circuits 1010/1012 of FIG. 10A-B, 1110/1112 of FIG. 11, and/or other circuits are used. In FIGS. 10A-B, 11 and 12, the motion componentry 214 controls the rotational and/or translational motion of the transducer array 210. Such control can be through a gear, a belt, a chain, a piston, a lead screw, a ball screw, a motor, a combination thereof, and/or other mechanism. Furthermore, electronic steering can be used in addition to and/or in alternative to the mechanical motion.

FIG. 13 shows a variation in which the optical imaging component 220 and the illumination component 218 are located outside of the housing 302. A second housing 1302 houses the optical imaging component 220 and the illumination component 218. In another instance, the second housing 1302 is omitted. In this example, the members 318 are also located outside of the housing 302. In another instance, the members 318 pass through the housing 302, as described above, and then through a material free region in the tip region 312 to the optical imaging component 220 and the illumination component 218. In another instance, the illumination component 218 is located outside of the housing 302, as shown in FIG. 13 or otherwise, and the optical imaging component 220 is located inside of the housing 302, as described herein or otherwise. In yet another instance, the optical imaging component 220 is located outside of the housing 302, as shown in FIG. 13 or otherwise, and the illumination component 218 is located inside of the housing 302, as described herein or otherwise.

In another variation, one or more of the members 318 can be routed outside of the conduit 316 and inside of the housing 302. Where less than all of the members 318 are routed as such, one or more of the members can be routed in the conduit 316, as described herein and/or otherwise, and/or outside of the housing 302, as described herein and/or otherwise.

The embodiments of FIGS. 3, 8, 9, 10A, 11, 12 and 13 can have different levels of integration. For example, in FIGS. 3, 8, 9, 10A, 11 and 12, the transducer array 210, the optical imaging component 220, the illumination component 218, and the (electrical and/or optical pathways) members 318 are all in the same housing 302. The members 318 can be part of the same cable or different cables therein, and the circuits for the optical imaging component 220 and the illumination component 218 can be part of a same circuit substrate (as shown in FIGS. 10A-B and 11) or different circuit substrates. In FIG. 12, in contrast, the optical imaging component 220, the illumination component 218 and the members 318 are integrated on the outside of the housing 302. The optical imaging component 220, the illumination component 218 are in a housing 1302, which can be considered a different housing attached to the housing 302, or housings 302 and 1302 can be considered sub-housings of a single housing. The members 318 are integrated with the probe 204 on the outside of the housing 302. Other levels of integration are also contemplated herein.

Figure 14:
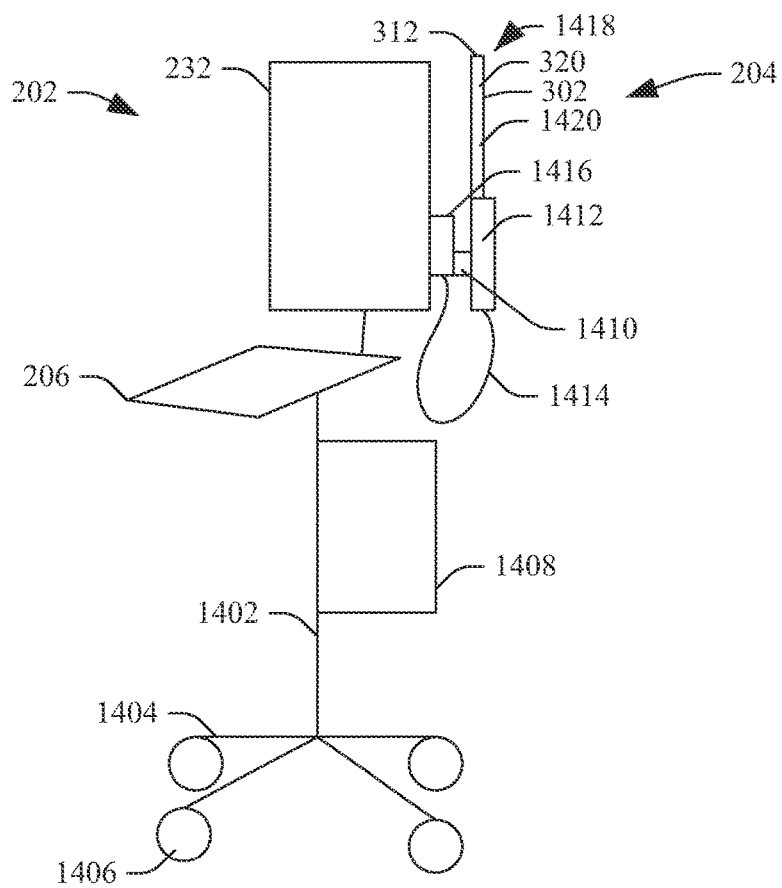
FIG. 14 illustrates an example of the ultrasound imaging system.

FIG. 14 illustrates an example of the ultrasound imaging system 202. In this example, the display 232 and the console 206 are separate devices attached to a mobile cart 1402, which includes a base 1404 with movers 1406 such as wheels, casters, etc. A portable energy source 1408 such as a rechargeable and/or non-rechargeable battery pack and/or other source supplies power for the system 202. A probe support 1410 is affixed to the cart 1402 and supports at least the probe 204. In another configuration, the ultrasound imaging system 202 rests on a table, desk, etc., and does not include movers and is not attached to a cart.

In the illustrated embodiment, the probe 204 is an endocavitary volumetric transducer with a handle 1412 and a cable 1414 that extends from the handle and includes a communications interface 1416 to console 206 at an end region of the cable. The probe 204 includes a shaft 1418 extending from an opposing end of the handle 1412 and including a first proximal region affixed to the handle and a second distal region including an acoustic window and enclosing the transducer array (not visible), the illumination component 218 (not visible), and the optical imaging component 220 (not visible).

Figure 15:
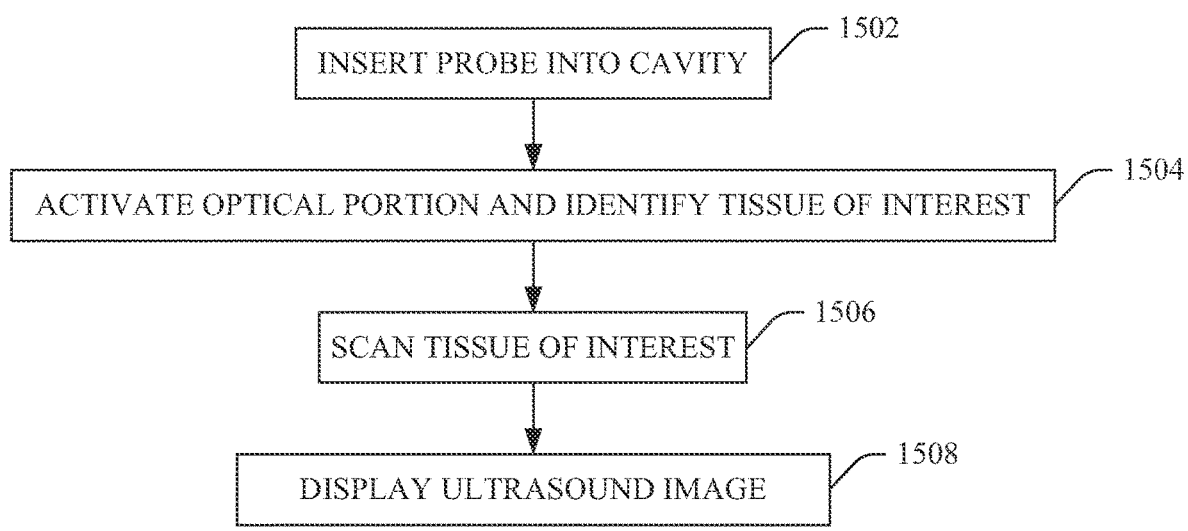
FIG. 15 illustrates an example method in accordance with an embodiment described herein.

FIG. 15 illustrates a method for employing the probe 204.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 1502, at least a sub-portion of the housing 302 is inserted into a cavity of a subject or object. As described herein, in one instance the probe 204 includes all of the transducer array 210, the illumination source(s) 218 and the optical sensor(s) 220 within the housing 312.

At 1504, the illumination source(s) 218 and the optical sensor(s) 220 are activated and used to locate tissue of interest. For example, with a colorectal examination, this may include using the illumination source(s) 218 and the optical sensor(s) 220 to locate cancer, a polyp and/or other tissue of interest.

At 1506, the transducer array 210 is activated to acquire ultrasound data for the identified tissue of interest.

At 1508, the acquired ultrasound data is processed and displayed.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging probe, comprising:
   a transducer array, including:
      one or more transducer elements;
   an illumination component;
   an optical imaging component; and
   an elongated housing with a long axis, the elongated housing including:
      a proximal end region affixed to a handle; and
      a distal end region with a tip region,
   wherein the elongated housing houses the transducer array, the illumination component, and the optical imaging component in the distal end region, and wherein the transducer array is configured to translate in a direction of the long axis.

2. The ultrasound probe of claim 1, wherein the illumination component and the optical imaging component are disposed in the tip region.

3. The ultrasound probe of claim 2, further including at least a second illumination component and at least a second optical imaging component disposed in the tip region.

4. The ultrasound probe of claim 2, further including at least a second illumination component and at least a second optical imaging component disposed inside of the housing outside of the tip region.

5. The ultrasound probe of claim 1, further comprising:
   a set of members, including electrically conductive members and optical routing members, extending within the housing and interfacing with the illumination component and the optical imaging component.

6. The ultrasound probe of claim 5, further comprising:
   a conduit in the housing that routes the set of members in the housing.

7. The ultrasound probe of claim 5, wherein the set of members extend from the proximal end region through the distal end region to the illumination component and the optical imaging component.

8. The ultrasound probe of claim 5, wherein the transducer array includes a first end affixed to a support and a second end, and further comprising:
   a first circuit affixed to the second end of the transducer array and including first contacts interfaced with the set of members; and
   a second circuit affixed at the tip region and including second contacts interfaced with the illumination component and the optical imaging component,
   wherein the set of members and the illumination and optical imaging components interface through the first and second circuits.

9. The ultrasound probe of claim 8, wherein the first and second contacts interface through physical contact.

10. The ultrasound probe of claim 8, wherein the first and second circuits interface through wireless communication.

11. The ultrasound probe of claim 1, wherein the illumination component includes at least one light emitting diode.

12. The ultrasound probe of claim 1, wherein the optical imaging component includes at least one of a still image camera, a video camera, or an optical fiber.

13. The ultrasound probe of claim 1, wherein the transducer array is configured to rotate about the long axis.

14. A method, comprising:
   receiving a first signal activating a light source and an optical sensor disposed in an ultrasound imaging section of an ultrasound probe in a cavity;
   acquiring optical data of a field of view in the cavity with the optical sensor, wherein the field of view is illuminated by light from the light source;
   generating an optical image with the optical data, wherein the optical image shows tissue of interest in the field of view;
   displaying the optical image;
   receiving a second signal activating an ultrasound transducer array disposed in the ultrasound imaging region of the ultrasound probe;
   rotating a transducer array disposed in the ultrasound imaging region of the ultrasound probe about a long axis of the probe;
   acquiring, while rotating the transducer array, ultrasound data of the tissue of interest in the field of view in the cavity with a transducer array disposed in the ultrasound imaging region of the ultrasound probe;
   generating an ultrasound image with the ultrasound data; and
   displaying the ultrasound image.

15. The method of claim 14, further comprising:
   concurrently displaying the optical image and the ultrasound image.

16. The method of claim 14, further comprising:
   alternating display of the optical image and the ultrasound image.

17. The method of claim 14, wherein the optical image shows second tissue of interest, and further comprising:
   acquiring second ultrasound data of the second tissue of interest in the field of view in the cavity with the transducer array disposed in the ultrasound imaging region of the ultrasound probe;
   generating a second ultrasound image with the second ultrasound data; and
   displaying the second ultrasound image.

18. The method of claim 14, further comprising:
   acquiring second optical data of second tissue of interest;
   generating a second optical image with the second optical data;
   displaying the second optical image;
   receiving a second signal activating an ultrasound transducer array disposed in the ultrasound imaging region of the ultrasound probe;
   acquiring second ultrasound data of the second tissue of interest in the second field of view in the cavity with the transducer array;
   generating a second ultrasound image with the second ultrasound data; and
   displaying the second ultrasound image.

19. An endocavitary volumetric transducer, comprising:
   a handle with a first wireless interface;
   a cable extending from the handle and including an interface to an ultrasound system at an end region of the cable;
   a shaft extending from an opposing end of the handle, the shaft, including:
      a proximal region affixed to the handle; and
      a distal region including an acoustic window and enclosing a transducer array, a light source, an optical imager, and a second wireless interface, wherein the first wireless interface and the second wireless interface are complementary wireless interfaces.

20. The endocavitary volumetric transducer of claim 19, wherein the first wireless interface and the second wireless interface are configured for communication between the light source and the optical imager.

* * * * *